US012576011B2

(12) United States Patent
Brewster et al.

(10) Patent No.: US 12,576,011 B2
(45) Date of Patent: Mar. 17, 2026

(54) MILK MINDER METHODOLOGIES AND SYSTEMS

(71) Applicant: Veon Brewster, Coral Springs, FL (US)

(72) Inventors: Veon Brewster, Coral Springs, FL (US); Emily Gray, Ottawa (CA); Bhavisha Parmar, Ottawa (CA); Rohan Thakar, Ottawa (CA); Aliasgar Morbi, Gurnee, IL (US)

( * ) Notice: Subject to any disclaimer, the term of this patent is extended or adjusted under 35 U.S.C. 154(b) by 696 days.

(21) Appl. No.: 17/952,361

(22) Filed: Sep. 26, 2022

(65) Prior Publication Data

US 2023/0097419 A1     Mar. 30, 2023

Related U.S. Application Data

(60) Provisional application No. 63/248,622, filed on Sep. 27, 2021.

(51) Int. Cl.
*A61J 9/00* (2006.01)
*B65D 79/02* (2006.01)
(Continued)

(52) U.S. Cl.
CPC ................. *A61J 9/00* (2013.01); *H04W 4/80* (2018.02); *A61J 2200/72* (2013.01);
(Continued)

(58) Field of Classification Search
CPC .. A61J 9/00; A61J 9/02; A61J 2200/72; A61J 2200/76; H04W 4/80; G01G 17/04;
(Continued)

(56) References Cited

U.S. PATENT DOCUMENTS 7,061,832 B1 *   6/2006   Lansing ..................... A61J 9/00
                                                              368/242
9,244,440 B2 *   1/2016   Pantchenko .............. G04F 3/06
                          (Continued)

FOREIGN PATENT DOCUMENTS

WO       WO-2020036572 A1 *   2/2020   ............. A47G 23/16

OTHER PUBLICATIONS

Machine translation of WO_2020036572 (Year: 2020).*
Computer translation of JP_2019_529864_A (Year: 2019).*
Computer translation of KR_2023_0067270_A (Year: 2023).*

*Primary Examiner* — Randy W Gibson

(57) ABSTRACT

A baby bottle management system is provided. The system includes a baby bottle composite monitor. The baby bottle composite monitor includes a temperature sensor. The monitor also includes a time measurement device. Further, the monitor includes a local visual annunciator. The monitor includes a display. The monitor also includes a local audible annunciator. The monitor further includes a speaker. The monitor also includes a communications module configured to allow communications between the baby bottle composite monitor and system users. The system further includes a baby bottle composite monitor strap designed to attach the baby bottle composite monitor to a baby bottle. The system also includes a baby bottle management system operating platform structured to allow system users to view, operate, manage, communicate, and control baby bottle management system data and operations from a mobile device, smart phone, tablet, computer, configurable and downloadable as a mobile application.

11 Claims, 6 Drawing Sheets

(51) Int. Cl.

| | |
|---|---|
| *G01G 17/04* | (2006.01) |
| *G01G 19/414* | (2006.01) |
| *G06Q 10/08* | (2024.01) |
| *H04W 4/80* | (2018.01) |
| *B01F 33/501* | (2022.01) |
| *G06Q 10/087* | (2023.01) |
| *G16H 20/60* | (2018.01) |

(52) U.S. Cl.
CPC ...... *A61J 2200/76* (2013.01); *B01F 33/50111* (2022.01); *B65D 79/02* (2013.01); *B65D 2203/12* (2013.01); *G01G 17/04* (2013.01); *G01G 19/4146* (2013.01); *G06Q 10/087* (2013.01); *G16H 20/60* (2018.01)

(58) Field of Classification Search
CPC .. G01G 19/414; G01G 19/4146; G01G 19/52; B65D 79/02; B65D 2203/12; B01F 33/50111; B01F 35/2021; B01F 35/5021; G16H 20/60; G06Q 10/087
See application file for complete search history.

(56)         References Cited

U.S. PATENT DOCUMENTS

| | | | | |
|---|---|---|---|---|
| 10,286,368 B2 * | 5/2019 | Deshpande | ............ | B65D 25/08 |
| 2014/0311239 A1 * | 10/2014 | Marjanovic | ............ | G01G 21/28 |
| | | | | 73/296 |
| 2015/0245723 A1 | 9/2015 | Alexander | | |
| 2016/0082165 A1 * | 3/2016 | Alvarez | .................. | A61M 1/06 |
| | | | | 604/74 |
| 2017/0300660 A1 * | 10/2017 | Ziv | ..................... | H04L 63/0435 |
| 2018/0197629 A1 | 7/2018 | Zhou | | |
| 2019/0189271 A1 | 6/2019 | Mintzer | | |
| 2021/0212901 A1 * | 7/2021 | Wood | ..................... | G01P 15/00 |

* cited by examiner

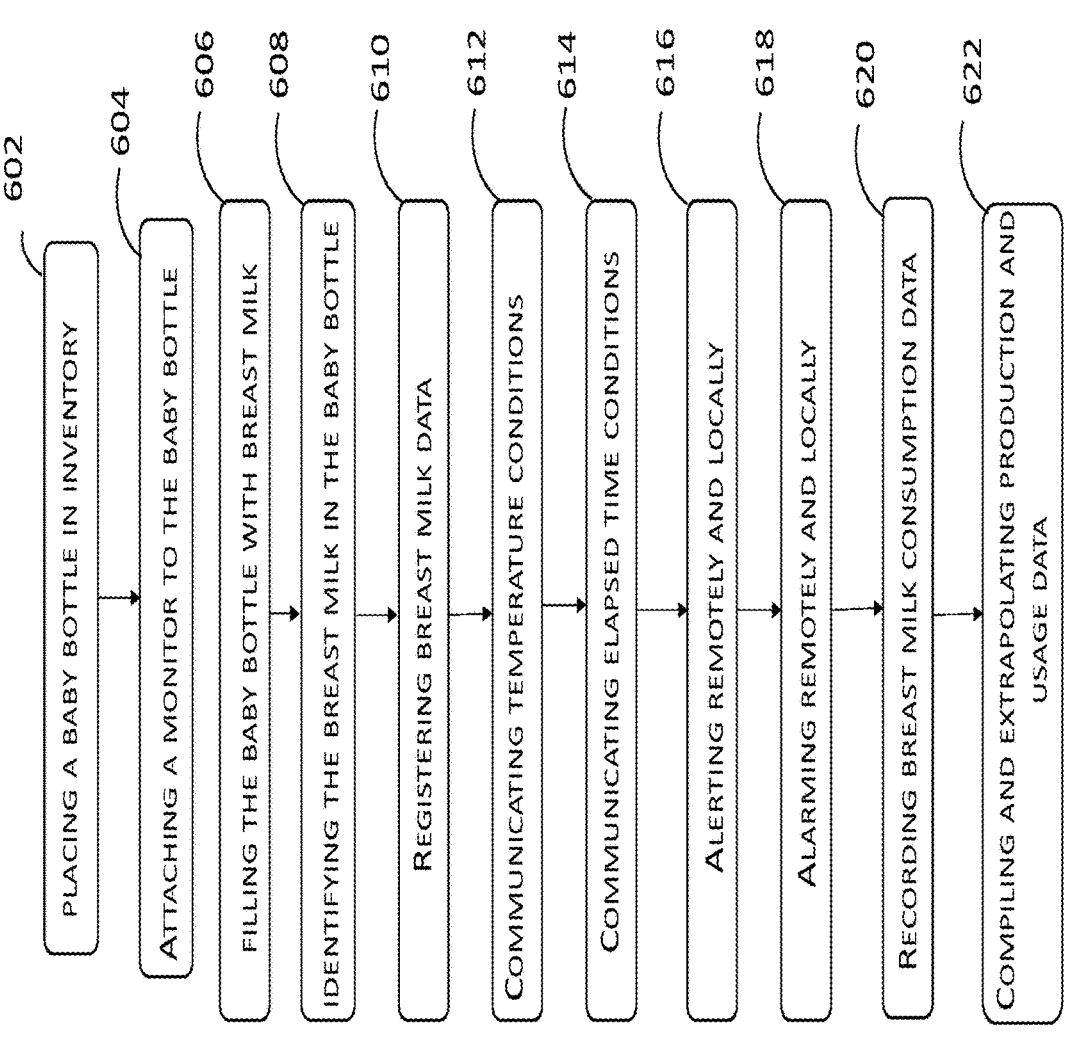

FIG. 6

602 — PLACING A BABY BOTTLE IN INVENTORY

604 — ATTACHING A MONITOR TO THE BABY BOTTLE

606 — FILLING THE BABY BOTTLE WITH BREAST MILK

608 — IDENTIFYING THE BREAST MILK IN THE BABY BOTTLE

610 — REGISTERING BREAST MILK DATA

612 — COMMUNICATING TEMPERATURE CONDITIONS

614 — COMMUNICATING ELAPSED TIME CONDITIONS

616 — ALERTING REMOTELY AND LOCALLY

618 — ALARMING REMOTELY AND LOCALLY

620 — RECORDING BREAST MILK CONSUMPTION DATA

622 — COMPILING AND EXTRAPOLATING PRODUCTION AND USAGE DATA

MILK MINDER METHODOLOGIES AND SYSTEMS

RELATED APPLICATIONS

This application claims priority to U.S. Provisional Application No. 63/248,622 filed Sep. 27, 2021. The entire contents of the above application are hereby incorporated by reference as though fully set forth herein.

FIELD OF THE INVENTION

The present invention relates to systems and methodologies to ensure the safety of pumped breast milk, and particularly to integrated milk minder methodologies and systems to be able to assist parents in an efficient and cost-effective way to utilize and optimize a supply of pumped breast milk and to keep their infants safe by using the pumped breast milk before it is no longer safe to consume.

COPYRIGHT NOTICE

BACKGROUND OF THE INVENTION

Previous attempts to create methods and systems utilizing reusable, convenient, cost-effective systems have been unsuccessful. In many instances, a variety of these previous attempts were cumbersome and depended on handwritten information on a bottle or on a bag containing the breast milk, and therefore the previous systems were typically non-reusable and/or non-sanitary. Reusability, and the ability to utilize mobile devices are features that were not contemplated by previous methods and systems. Further, current systems and processes, due to their non-reusability, make these current systems and processes very expensive and time consuming.

Many of previously used systems relied on best guess estimates of when a baby bottle of breast milk was taken out of a refrigerator and left at room temperature. Due to the time required to produce breast milk wasting milk due to inaccurate oversight of the milk proves frustrating, time consuming, and expensive.

Often parents undertake their own methods of estimating when baby bottles of breast milk are left out of the refrigerator. Quite often parents forget to share with one another their methodologies and this confusion often results in breast milk going to waste due to poor milk management.

Accordingly, there is an established need for integrated Milk Minder methodologies and systems which solve at least one of the aforementioned problems. Further, there is an established need for integrated Milk Minder systems, having various forms, that help a user to store pumped breast milk, monitor upcoming expiration of stored breast milk, and to keep infants safe.

SUMMARY OF THE INVENTION

According to an aspect of the present invention, an integrated Milk Minder system is presented. The system includes monitoring and alerting devices which attach to individual pumped breast milk containers. The system also includes visual status annunciation mechanisms attached to the monitoring and alerting devices. The system includes wireless communication devices attached to the monitoring and alerting devices which are configured to allow the individual breast milk container monitoring and alerting devices to communicate via a mobile application providing system users real-time status of the individual pumped breast milk containers.

A baby bottle management system is provided. The system includes a baby bottle composite monitor. The baby bottle composite monitor includes a temperature sensor. The monitor can also include a time measurement device. Further, the monitor can include a local visual annunciator. The monitor can include a display. The monitor can also include a local audible annunciator. The monitor can further include a speaker. The monitor also includes a communications module configured to allow communications between the baby bottle composite monitor and system users. The system further includes a baby bottle composite monitor strap designed to attach the baby bottle composite monitor to a baby bottle. The system also includes a baby bottle management system operating platform structured to allow system users to view, operate, manage, communicate, and control baby bottle management system data and operations from a mobile device, smart phone, tablet, or a computer, and wherein the baby bottle management system operating platform is configurable to be downloaded and used as a mobile application and wherein the baby bottle management system operating platform utilizes algorithms to determine how long breast milk or baby formula kept in the baby bottle is safe for consumption.

The system can include a plurality of baby bottle composite monitors and a corresponding plurality of baby bottles.

In embodiments, the baby bottle composite monitor can include an accelerometer, the accelerometer configured to detect three-dimensional movement and positioning of the baby bottle to which the baby bottle composite monitor is attached.

In embodiments, the system can include load cells, the load cells configured to automatically detect amounts of fluid consumed and added to the baby bottle.

In embodiments, the system can include a baby bottle composite monitor which includes an electronic level, the electronic level configured to detect angle to horizontal that a baby bottle is oriented to provide indication of when a baby bottle is on its side or is being utilized to feed an infant.

In embodiments, the baby bottle composite monitor can include a GPS tracking device.

In embodiments the system can include a bar code scanner, and bar codes on baby bottles designed to identify breast milk or baby formula origin information and to track information within the baby bottle management system.

In embodiments, the system can include a charging station, the charging station configured to charge the baby bottle composite monitor wirelessly or through contact charging.

In embodiments, the system can include Wi-Fi, Bluetooth®, and Personal Area Network (PAN) combined communications capabilities and configured to allow leap frogging communications between other wireless devices to allow enhanced communications between the baby bottle composite monitor and the baby bottle management system operating platform.

In embodiments, the system can include the baby bottle composite monitor which includes LED lights configured to illuminate in a plurality of colors and wherein the plurality of colors correlate to determined status of breast milk or baby formula within the baby bottle.

In an aspect, a computer implemented method for safely managing breast milk inventory is presented. The method includes the steps of placing in inventory a baby bottle; filling the baby bottle with breast milk; identifying the breast milk in the baby bottle; registering data associated with the breast milk in the baby bottle into a baby bottle management system; attaching a baby bottle composite monitor to the baby bottle; communicating temperature conditions from the baby bottle composite monitor to the baby bottle management system with a baby bottle management system operating platform; communicating elapsed time for a plurality of conditions from the baby bottle composite monitor to the baby bottle management system with a baby bottle management system operating platform; alerting remotely and locally by the baby bottle composite monitor existing breast milk safety status; alarming remotely and locally by the baby bottle composite monitor upcoming and existing breast milk safety status; and recording breast milk consumption data within the baby bottle management system.

In yet another aspect, computer system configured to safely manage breast milk inventory is presented, the system including a non-transitory computer readable medium coupled to a processor, the processor configured to place in inventory a baby bottle; fill the baby bottle with breast milk; identify the breast milk in the baby bottle; register data associated with the breast milk in the baby bottle into a baby bottle management system; attach a baby bottle composite monitor to the baby bottle; communicate temperature conditions from the baby bottle composite monitor to the baby bottle management system with a baby bottle management system operating platform; communicate elapsed time for a plurality of conditions to and from the baby bottle composite monitor to and from the baby bottle management system with a baby bottle management system operating platform; alert remotely and locally by the baby bottle composite monitor existing breast milk safety status; alarm remotely and locally by the baby bottle composite monitor upcoming and existing breast milk safety status; and record breast milk consumption data within the baby bottle management system.

In embodiments of the system, monitoring, alerting, and management of a plurality of baby bottles with breast milk are carried out with temperature sensors, horizontal and vertical displacement sensors, GPS sensors, local visual annunciators, wireless communications modules, all incorporated into a device configured to be incorporated into one component which is designed to be attached to baby bottles with a band or strap. The component can be structured to be roughly the size of a wristwatch face which can be arranged to be held onto a baby bottle with a variety of straps or bands and designed to be water resistant and operable in a variety of ambient temperature environments.

In embodiments, the system can incorporate mobile Apps which can be configured to be in real time communication with users of the App which can indicate the condition of a plurality of baby bottles with breast milk in a plurality of locations, for example, baby diaper bag, nursery, office, home, stroller bag, or other locations where parents or the infants utilizing the breast milk sleep, eat, rest, play, or otherwise are cared for.

In embodiments, the system can include local and remote elapsed time indicators and remaining time to use breast milk in each particular baby bottle.

In embodiments, the system can include a local LED status indicator, wherein the status indicator can include time remaining on the bottle for safe use, a color status indicator configured to alert local users based on a red, orange, yellow, purple, blue, or green lights to show a user condition of the contents of the baby bottle.

In embodiments, the system can include an accelerometer configured to detect bottle movement and bottle angle to horizon such that the system can detect when a baby bottle is in use.

In embodiments, the system can include charging ports to include USB and mobile device charging connections.

In embodiments, the system can include Wi-Fi, Bluetooth®, and PAN communications modules within a composite sensor attachable to a plurality of baby bottles to provide communication capabilities between the plurality of baby bottles and the system communications platforms.

In embodiments, the system can include load cells, the load cells arranged such that the amount of breast milk consumed is accurately and automatically recorded and can be used for breast milk usage metric data.

In embodiments, the system can allow manually and automatically setting time frames for acceptable breast milk usage based on ambient temperature and elapsed time at ambient temperature.

In embodiments, the system can include audible annunciation devices on baby bottles, on composite sensors, on or near baby bottle storage areas, baby bottle refrigerators, and on mobile devices such that time alerts, change of status of breast milk, count down of acceptable time remaining on breast milk in baby bottles, can be audibly heard by systems users on their mobile device, computer, on the local composite sensor on the baby bottle, and the alerts can be programmed to increase in frequency based on the time sensitive nature of breast milk about to expire and not being safe to use.

In embodiments, the system can include LED numerical readout displays allowing system user to see remaining time left on a baby bottle with breast milk safe for consumption.

In embodiments, a method for maintaining breast milk safe for consumption can include an APP on a mobile device and a software program downloadable and able to be used in counting available baby bottles with breast milk in inventory, adding new baby bottles, removing baby bottles once breast milk has been consumed or milk is no longer safe for consumption, measuring ambient temperature of a baby bottle containing breast milk, measuring breast milk temperature, calculating amount of elapsed time a baby bottle with breast milk is frozen, refrigerated, or exposed to ambient temperature, determining acceptable remaining time on baby bottles containing breast milk wherein the milk is safe for consumption, displaying alpha numeric information describing condition of breast milk and milk characteristic information, annunciating with visual and audible mechanisms communication to system users on mobile devices, computers, baby bottle storage areas, on baby bottles milk condition and available time left for safe consumption, alerting system users on mobile devices, computers, baby bottle storage areas, on baby bottles milk condition and available time left for safe consumption, compiling breast milk usage data, reporting milk usage data, and recording milk usage data.

In embodiments, the system can include data capturing mechanisms to identify source of breast milk and donor information.

In embodiments, the system can include mechanisms to capture breast milk data with bar code information capturing milk characteristic information and donor information.

In embodiments, the system can include temperature sensors, time measurement devices, accelerometers, load cells, audible and visual annunciation devices, alarming devices, alerting devices, deployed onto a plurality of baby bottles and baby formula and breast milk containers and dispensers, configured to track consumption data, time exposures to a plurality of environmental parameters, such as temperature, humidity, radiant heat absorption, and elapsed time that baby milk is exposed to a plurality of factors and designed to be in two way communication with supervisory mobile application platforms. Further, in these embodiments, these system components and algorithms can be designed to manage on a real time basis, baby formula, breast milk, baby food, and infant drinking fluids usage to prevent consumption of unsafe breast milk and to manage an infant's milk consumption for dietary tracking purposes.

In embodiments, the system can alert and provide advance notices of when to plan for future breast milk production in order to maintain calculated baby consumption.

In embodiments, the system can be configured to provide tracking data and usage data for quality control parameters such as utilization of breast milk percentages, breast milk wastage, breast milk production statistics, individual infant baby milk consumption parameters such as timing of feedings, volume of milk consumed during feedings, extrapolation predictions for future milk consumption needs.

In embodiments, the system can include automatic tracking data for the plurality of baby bottles entered into the system.

In embodiments, the system can include algorithms to calculate bacteria growth in baby bottles and in the breast milk or baby formula.

In embodiments, the system can include data and control transmissions between baby bottle sensors and communications platforms being used by system users such that over ride alert notifications can be pushed out by a user on a mobile app or on a software platform.

In embodiments, the system can include automatic pairing between baby bottle sensors and localized system interfaces such that baby bottle sensors and annunciation devices can allow bidirectional communication between sensors, software, firm ware and hardware.

In embodiments, the system can include auto identification information on each baby bottle monitoring device such that by touching or engaging with an interface on the baby bottle monitoring device, breast milk origin and usage information can be given audibly. Information such as who the donor is for the breast milk, when the breast milk was produced, how long it was frozen, refrigerated, and how long the baby bottle has been in the localized environment can be obtained audibly and visually.

In embodiments, the system can automatically detect when a baby is feeding based on the angle of the bottle and the amount of time spent in that position, as well as consumption data based on load cells attached to the baby bottle, baby bottle monitoring device, or baby bottle storage rack. Further, the system can include baby bottle storage racks wherein the baby bottle monitors and/or sensors can be inductively charged when the baby bottles are secured in the storage racks.

In embodiments, the system can include remote and local annunciation capabilities, audible, visual, and vibration, which can be initiated automatically and manually and can include text messages and telephone calls to local, remote, and third parties.

In embodiments, the system can include data logging, chronological data logging, run the data through algorithms designed to extrapolate future usage, future supply needs, consumption usage formulated to allow medical diagnosis of consumption data including time between feedings, amounts consumed during feedings, interfacing data with infant growth charts, and predicting future infant growth and needs.

In embodiments, the system can alert users of how much baby formula or milk is left in a bottle, and what how soon a new bottle needs to be ready for the infant.

In embodiments, the system can link to other wireless devices and "leap-frog" communications between the wireless devices and communicate with the operating system platform on a mobile app or on an operating station, laptop, or other computing device.

In embodiments, the system can include time measurement capabilities within the operating platform and utilizing elapsed time measurements to send alerts, alarms, and notifications to the system and to the composite monitor.

These and other features and advantages will become apparent from the following detailed description of illustrative embodiments thereof, which is to be read in connection with the accompanying drawings.

BRIEF DESCRIPTION OF THE DRAWINGS

The features and advantages of the present invention will be better understood when the Detailed Description of the Preferred Embodiments given below is considered in conjunction with the figures provided.

FIG. 6 is a flow chart displaying method steps taken with a mobile application of an embodiment of the present invention.

DETAILED DESCRIPTION

The following detailed description is exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
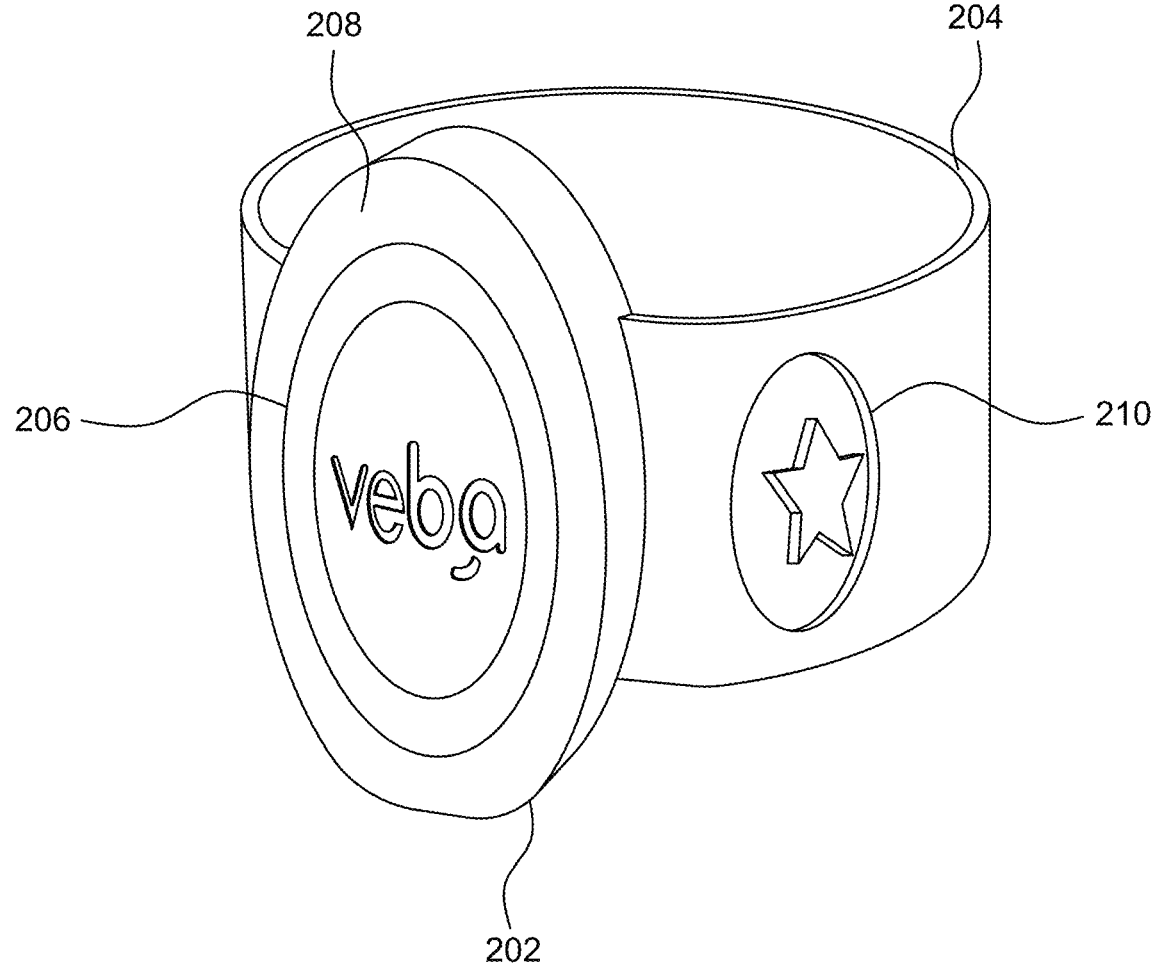
FIG. 1 is a top right hand perspective view of an embodiment of the present invention showing a baby bottle composite monitor.

Referring initially to FIG. 1, a top front right hand perspective view of a baby bottle composite monitor 202 with a strap 204 is shown. The monitor 202 can include a illuminating source 208 such as a LED 208 which can be configured to light up in a constant or flashing light fashion to indicate a particular status or alarm setting. The light can be different colors to correlate to a particular status, for instance green for good or yellow for caution. The monitor 202 can include a display 214 for indicating a message and for additional annunciation features. The monitor 202 can also include a speaker 206 configured to provide audible messages, advisories, or warnings. The strap 204 or band 204 can include particular identification markings 210 or locations on the band 204 to insert unique identifiers onto a specific baby bottle 300.

Figure 2:
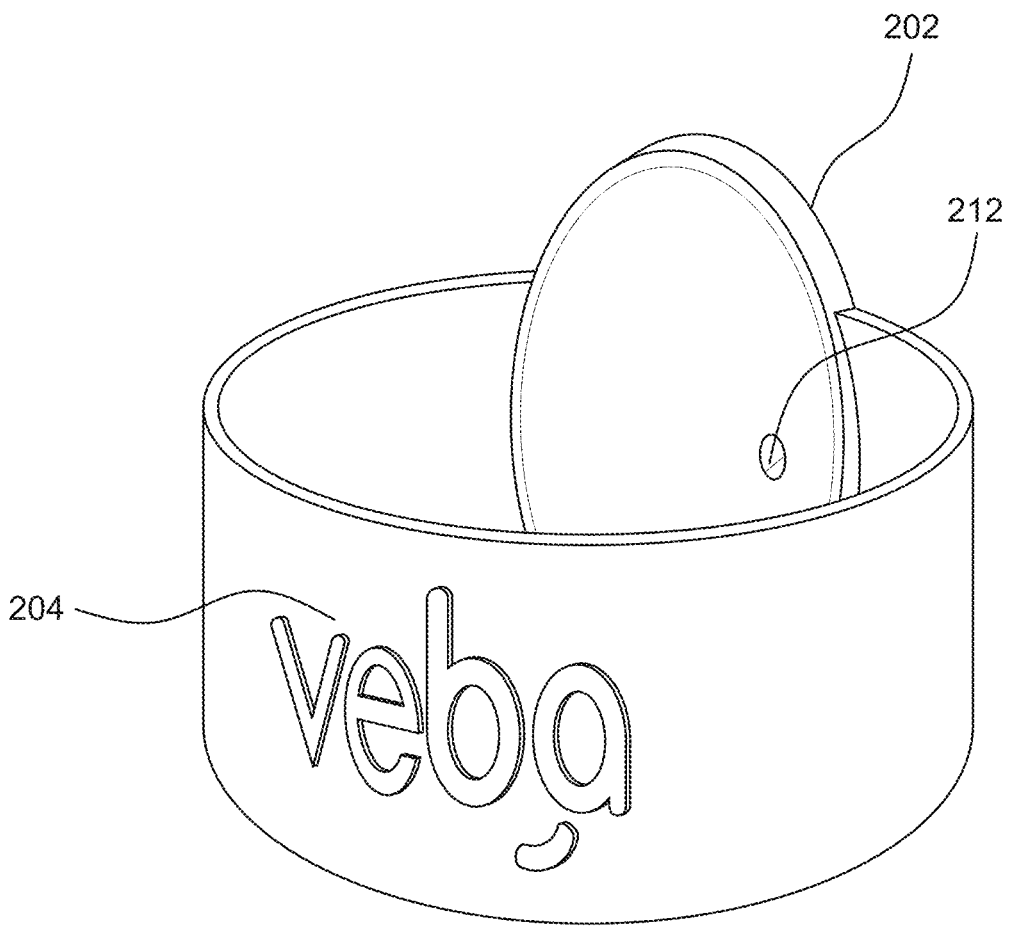
FIG. 2 is a back perspective view of an embodiment of the present invention showing a baby bottle composite monitor.

FIG. 2 shows a top back side perspective view of a baby bottle composite monitor 202 with a band 204 attached. The monitor 202 can include connection points 212 on a back side of the monitor 202. The connection points 212 can be configured to allow charging of the monitor 202 with standard charging adaptors of mobile devices and can also be designed to allow transfer of data to and from the monitor 202 to external devices (not shown) or to data communications connections to transmit data to the baby bottle management system operating platform. The band 204 can be configured to be formed as a unitary piece with the monitor 202 or the band 204 can be structured to be attached to the monitor 202 with a plurality of connection devices such as snap on-off, click on-off, Velcro, magnetic, curved plastic memory spring action, standard wristwatch connectors, or twist-tie.

Figure 3:
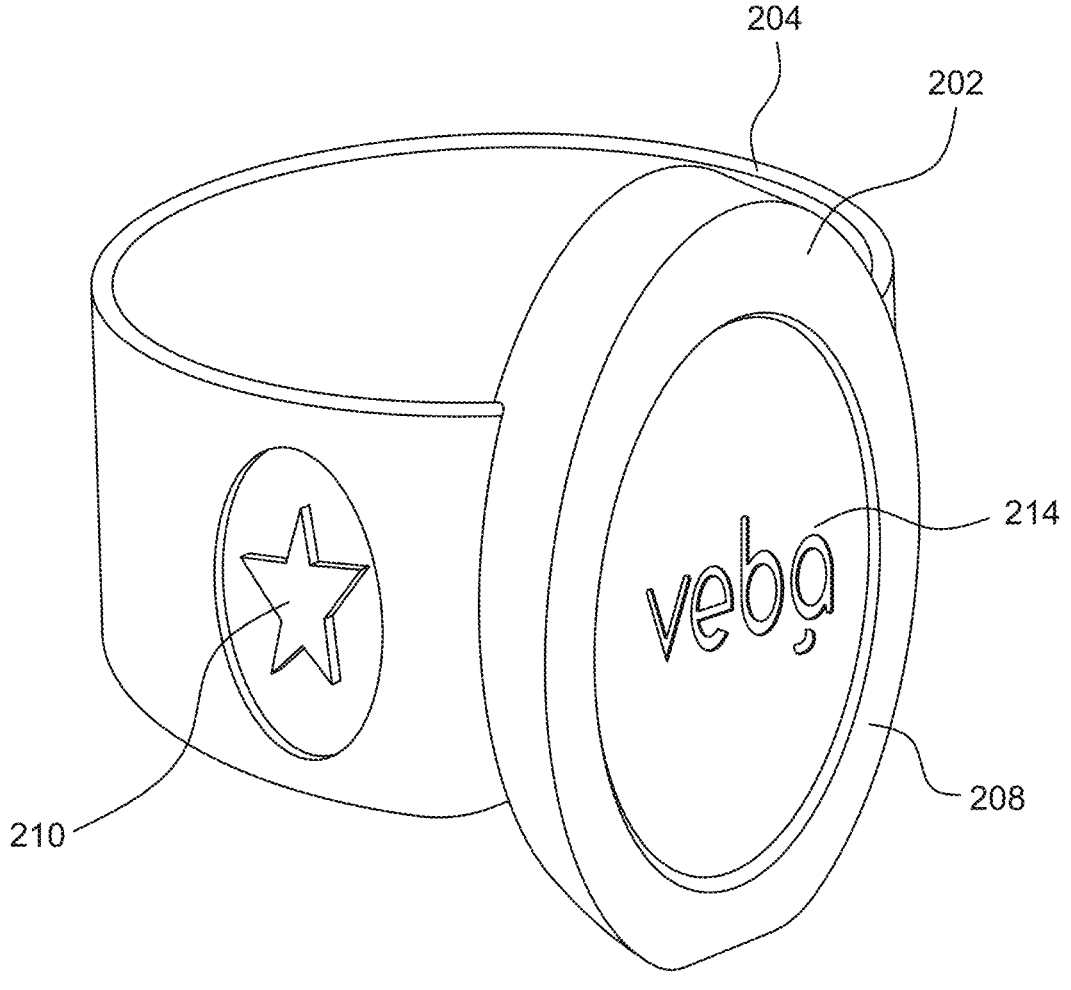
FIG. 3 is a top left hand perspective view of an embodiment of the present invention showing a baby bottle composite monitor.

Turning to FIG. 3, an embodiment of the composite monitor 202 is shown. The monitor 202 can include an ambient temperature sensor internal to a housing of the monitor 202. The monitor 202 can also include a display 214. The display 214 configured to display messages, warnings, and alerts as well as baby bottle management usage and anticipated future action advisories such as how much longer the breast milk in a baby bottle that is being measured is safe for consumption, how much breast milk remains in a baby bottle, what the current ambient temperature is, when breast milk production needs to commence in order to maintain extrapolated usage rate, error messages, and user information. The monitor can further include a speaker 206, the speaker 206 designed to annunciate, alarm, alert, and convey audible messages and advisories to system users. The monitor 202 can include LED lights 208 arranged to visually alert, alarm, and indicate to system users' condition of breast milk in the baby bottle and system messages.

Figure 4:
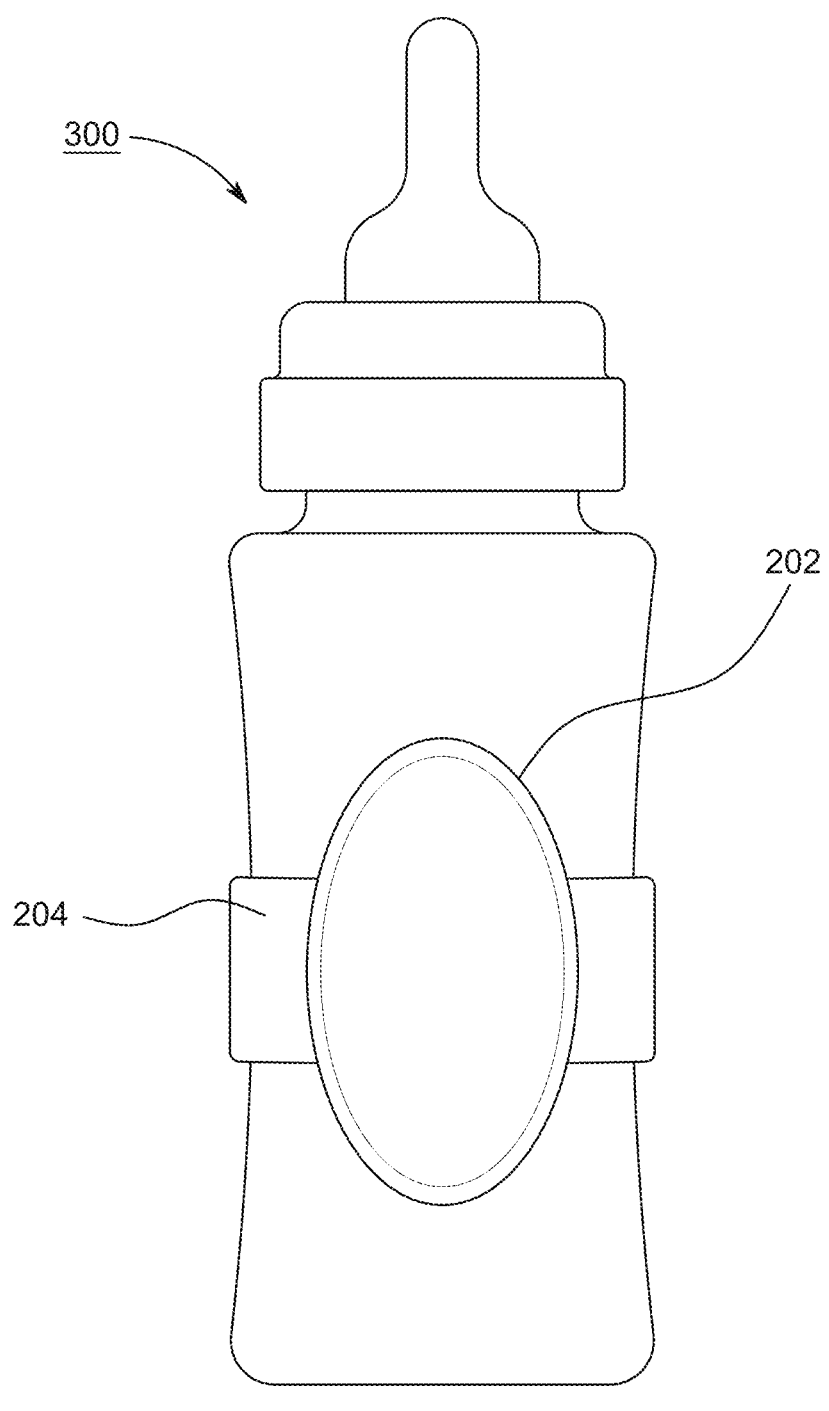
FIG. 4 is an embodiment of the present invention showing a baby bottle composite monitor attached to a baby bottle in accordance with an embodiment of the present invention.

FIG. 4 shows a monitor 202 attached to a baby bottle 300 with a strap 204. The monitor 202 can house temperature sensors, electronic level sensors, accelerometers, time measurement devices, lights, speakers, displays, charging connections, bar code scanner, GPS locator device, designed to capture environmental data and status of breast milk in the baby bottle and track consumption and monitor to provide for safe consumption conditions for a baby. In embodiments not shown, the system can include charging stations wherein a plurality of monitors 202 can be simultaneously charged with wired or wireless devices, such as induction charging, with the monitors 202 attached to baby bottles 300 or not attached. The charging station can charge a bank of monitors remotely. The system can also include load cells, arranged to be able to automatically determine breast milk consumption based on weight differences between feeding of the contents of the baby bottle.

Figure 5:
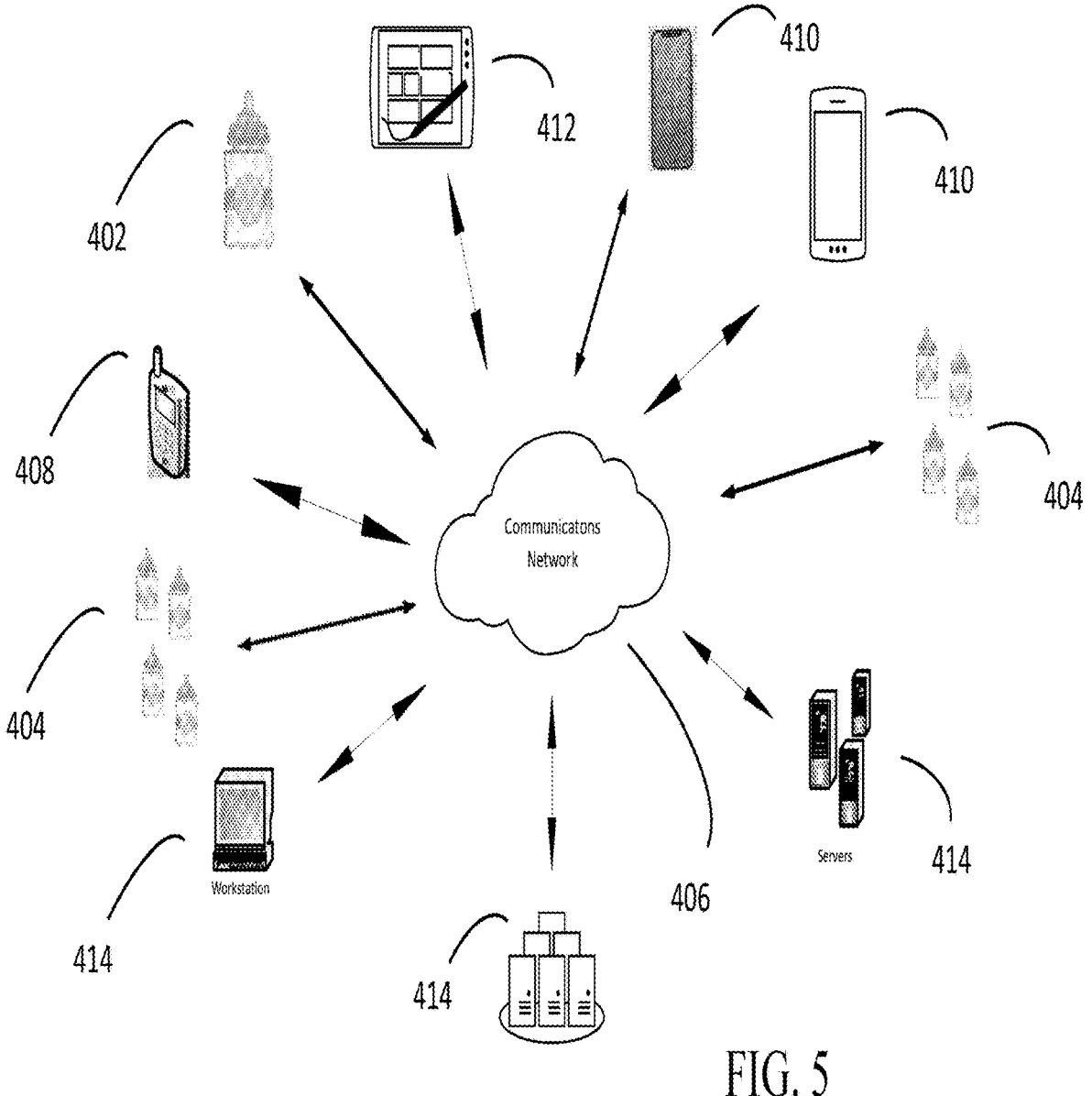
FIG. 5 is a display of the various communication pathways system components can communicate amongst themselves and with other computing devices in accordance with an embodiment of the present invention.

FIG. 5 displays communication pathways and system user touch points in an embodiment of the present invention. As best seen in FIG. 5, a composite monitor 202 attached to a baby bottle 300 and 402 or a plurality of monitors 202 attached to their corresponding baby bottles 404 can be in real time communication through existing wireless systems, Wi-Fi, local hotspots, Bluetooth®, Personal Area Networks (PAN), smart phones 408, smart devices 410, wireless mobile devices 412, and other computer systems 414 wireless and wired communications systems 406 and allow system users to control, access, manage, and interact with embodiments of the baby bottle management system through a baby bottle management system operating platform. The operating platform can be deployed onto a mobile device 410 or a smartphone 408 or a computer system 414 as a downloadable mobile App. The mobile App can allow system users to manage the baby bottle management system through a baby bottle management system operating platform and allow up to date real time information on conditions of the plurality of plurality of monitors 202 attached to their corresponding baby bottles 404, allow the system to push out condition alerts to the monitors 202, and allow feedback from the monitors 202 to the baby bottle management system through a baby bottle management system operating platform and update condition information of the baby bottles. Further, the system can record usage data, using algorithms, extrapolate future usage and provide management data such as time left for safe consumption of breast milk in particular baby bottles and provide notifications of when future breast milk production needs to take place in order to meet anticipated and calculated future usage demands.

FIG. 6. describes steps of a method in an embodiment of the present invention which allows system users to safely manage breast milk inventory. The system initially can begin entering baby bottles 602 into the system inventory in order to begin allocation of breast milk in particular baby bottles. The system can then tracking baby bottle conditions by attaching a monitor to the baby bottle 604. In embodiments of the invention a plurality of baby bottles with a plurality of corresponding monitors 202 can be managed by the system in maintaining real time condition of each baby bottle and the ambient environmental conditions. Once the monitor 202 is attached to its corresponding baby bottle 300, the system can begin logging data on that baby bottle's ambient environment. The system can then allocate breast milk in each baby bottle by filling the baby bottles with breast milk 606. The system can then begin identifying the breast milk in each baby bottle 608. The system can also begin registering breast milk data 608 such as donor, when produced, how much was produced, and if the breast milk was frozen prior to placing the breast milk in the bottles. The system can begin communicating between monitors 202 and the system, temperature conditions ambient to a specific baby bottle 612. The system can also begin communicating elapsed time conditions of each baby bottle 614 such as how long the baby bottle has been exposed to ambient temperatures greater than 77 F, or how much longer the breast milk in a specific baby bottle can be used to feed an infant and be consumed safely, how long a baby bottle has been titled on its side or in a feeding position, and how long specific time frames have existed between feedings for a specific infant. The system carries out supervisory roles by alerting remotely and locally potentially unsafe conditions for the breast milk, how much time is left before expiration, how much breast milk is available in total at a given location, and how much time remains before breast milk production needs to occur.

Continuing with FIG. 6, the system can also carry out safety functions by alarming remotely and locally when unsafe conditions exist with breast milk 618. The system can further enhance breast milk management functions by recording breast milk consumption data 620. Data such as how much was consumed, how many feedings, how much time elapsed between feedings, how much breast milk is anticipated to be consumed based on past historical data and extrapolation of the growth of an infant. Therefore, the system can accomplish refined managerial functions by compiling and extrapolating production and usage data 622.

In embodiments of the invention, the system can include materials such as rubber, plastics, LED lights, wireless transmitters, and composites which can act as visual indication devices.

In embodiments, the system can include tracking mechanisms configured to track formula bottles and track breast milk received from donation centers.

In embodiments, the system can include exterior temperature sensors to alert system users if the breast milk containers are frozen, refrigerated, or in ambient temperature.

In embodiments, the system can include level indication sensors and load cells to alert system users if breast milk is being fully consumed.

In embodiments, the system can include data calculation algorithms for infant formula or beverages with expiration dates.

In some embodiments, the method or methods described above may be executed or carried out by a computing system including a tangible computer-readable storage medium, also described herein as a storage machine, that holds machine-readable instructions executable by a logic machine (i.e. a processor or programmable control device) to provide, implement, perform, and/or enact the above described methods, processes and/or tasks. When such methods and processes are implemented, the state of the storage machine may be changed to hold different data. For example, the storage machine may include memory devices such as various hard disk drives, CD, flash drives, cloud storage, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

The present invention has been described with reference to the preferred embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

What is claimed is:
1. A baby bottle management system comprising:
a baby bottle composite monitor;
  wherein the baby bottle composite monitor comprises;
    a temperature sensor;
    a local visual annunciator;
    a local audible annunciator;
    a communications module configured to allow communications between the baby bottle composite monitor and system users, wherein the communications includes changing visual indications, wherein the changing visual indications includes color changes and time of illumination changes;

a baby bottle composite monitor strap designed to attach the baby bottle composite monitor to a baby bottle;

a baby bottle management system operating platform structured to allow system users to view, operate, manage, communicate, and control baby bottle management system data and operations from a mobile device, smart phone, tablet, or a computer, and wherein the baby bottle management system operating platform is configurable to be downloaded and used as a mobile application and wherein the baby bottle management system operating platform utilizes algorithms to determine how long breast milk or baby formula kept in the baby bottle is safe for consumption.

2. The system of claim 1, wherein the baby bottle composite monitor includes a time measurement device and a speaker.

3. The system of claim 1, further comprising a plurality of baby bottle composite monitors and a corresponding plurality of baby bottles.

4. The system of claim 1, wherein the baby bottle composite monitor includes an accelerometer, the accelerometer configured to detect three-dimensional movement and positioning of the baby bottle to which the baby bottle composite monitor is attached.

5. The system of claim 1, further comprising load cells, the load cells configured to automatically detect amounts of fluid consumed and added to the baby bottle.

6. The system of claim 1, wherein the baby bottle composite monitor includes an electronic level, the electronic level configured to detect angle to horizontal that a baby bottle is oriented to provide indication of when a baby bottle is on its side or is being utilized to feed an infant.

7. The system of claim 1, wherein the baby bottle composite monitor includes a GPS tracking device.

8. The system of claim 1, further comprising a bar code scanner, and bar codes on baby bottles designed to identify breast milk or baby formula origin information and to track information within the baby bottle management system.

9. The system of claim 1, further comprising a charging station, the charging station configured to charge the baby bottle composite monitor wirelessly or through contact charging.

10. The system of claim 1, wherein the communications module includes Wi-Fi, Bluetooth, and Personal Area Network (PAN) combined communications capabilities and configured to allow leap frogging communications between other wireless devices to allow enhanced communications between the baby bottle composite monitor and the baby bottle management system operating platform.

11. The system of claim 1, wherein the baby bottle composite monitor includes LED lights configured to illuminate in a plurality of colors and wherein the plurality of colors correlate to determined status of breast milk or baby formula within the baby bottle.

* * * * *